United States Patent [19]
Mickley et al.

[11] Patent Number: 5,961,536
[45] Date of Patent: Oct. 5, 1999

[54] CATHETER HAVING A VARIABLE LENGTH BALLOON AND METHOD OF USING THE SAME

[75] Inventors: Timothy J. Mickley, Elk River; Steven P. Mertens, New Hope; Christopher R. Larson, St. Paul; Chad G. Harris, Big Lake; John H. Carlson, II, Zimmerman, all of Minn.

[73] Assignee: SciMed Life Systems, Inc., Maple Grove, Minn.

[21] Appl. No.: 08/950,520

[22] Filed: Oct. 14, 1997

[51] Int. Cl.$^6$ .................................................. A61M 25/10
[52] U.S. Cl. ........................ 606/194; 606/108; 606/192; 604/96
[58] Field of Search .................................. 606/194, 192, 606/108, 193; 604/96

[56] References Cited

U.S. PATENT DOCUMENTS

| | | | |
|---|---|---|---|
| 3,896,815 | 7/1975 | Fettel et al. | 128/348 |
| 4,240,433 | 12/1980 | Bordow | 128/347 |
| 4,349,033 | 9/1982 | Eden | 128/660 |
| 4,479,497 | 10/1984 | Fogarty et al. | 128/344 |
| 4,493,711 | 1/1985 | Chin et al. | 604/271 |
| 4,526,175 | 7/1985 | Chin et al. | 128/344 |
| 4,564,014 | 1/1986 | Fogarty et al. | 128/344 |
| 4,606,347 | 8/1986 | Fogarty et al. | 128/344 |
| 4,630,609 | 12/1986 | Chin | 128/344 |
| 4,650,466 | 3/1987 | Luther | 604/95 |
| 4,744,366 | 5/1988 | Jang | 128/344 |
| 4,771,776 | 9/1988 | Powell et al. | 128/344 |
| 4,779,611 | 10/1988 | Grooters et al. | 128/4 |
| 4,820,270 | 4/1989 | Hardcastle et al. | 604/96 |
| 4,848,343 | 7/1989 | Wallsten et al. | 128/343 |
| 4,863,440 | 9/1989 | Chin | 604/271 |
| 4,875,480 | 10/1989 | Imbert | 128/343 |
| 4,958,634 | 9/1990 | Jang | 606/194 |
| 5,002,532 | 3/1991 | Gaiser et al. | 604/101 |
| 5,002,558 | 3/1991 | Klein et al. | 606/192 |
| 5,019,042 | 5/1991 | Sahota | 604/101 |
| 5,047,045 | 9/1991 | Arney et al. | 606/194 |
| 5,049,131 | 9/1991 | Deuss | 604/96 |
| 5,071,406 | 12/1991 | Jang | 604/96 |
| 5,074,845 | 12/1991 | Miraki et al. | 604/101 |
| 5,090,958 | 2/1992 | Sahota | 604/98 |
| 5,116,318 | 5/1992 | Hillstead | 604/96 |
| 5,137,512 | 8/1992 | Burns et al. | 604/96 |
| 5,147,377 | 9/1992 | Sahota | 606/194 |
| 5,160,321 | 11/1992 | Sahota | 604/96 |
| 5,163,927 | 11/1992 | Woker et al. | 604/271 |
| 5,178,608 | 1/1993 | Winters | 604/99 |
| 5,192,297 | 3/1993 | Hull | 606/195 |
| 5,217,434 | 6/1993 | Arney | 604/99 |
| 5,226,889 | 7/1993 | Sheiban | 604/101 |
| 5,246,421 | 9/1993 | Saab | 604/96 |
| 5,257,974 | 11/1993 | Cox | 604/96 |
| 5,259,847 | 11/1993 | Trambert | 604/164 |
| 5,275,622 | 1/1994 | Lazarus et al. | 623/1 |
| 5,304,135 | 4/1994 | Shonk | 604/101 |
| 5,312,430 | 5/1994 | Rosenbluth et al. | 606/192 |
| 5,342,305 | 8/1994 | Shonk | 604/101 |
| 5,342,307 | 8/1994 | Euteneuer et al. | 604/103 |

(List continued on next page.)

*Primary Examiner*—Michael H. Thaler
*Attorney, Agent, or Firm*—Crompton, Seager & Tufte, LLC

[57] ABSTRACT

A variable length balloon catheter is provided. The balloon catheter includes a catheter shaft having a distal portion, a balloon and an adjustment device. The balloon is in fluid communication with a distal end of the catheter shaft. The adjustment device includes an outer sleeve and an attachment structure. The outer sleeve is configured to be generally co-axially received over the distal portion of the catheter shaft and includes a distal end configured to restrict inflation proximal the distal end. Further, the outer sleeve is configured such that at least a portion of the outer sleeve is slidable relative to the distal portion of the catheter shaft such that a distal end of the outer sleeve relative to the balloon can be varied. The attachment structure is similarly disposed at the distal portion of the catheter shaft and is configured to selectively secure at least a portion of the outer sleeve to the distal portion of the catheter shaft such that the outer sleeve will not move upon inflation of the balloon.

25 Claims, 4 Drawing Sheets

U.S. PATENT DOCUMENTS

| | | | |
|---|---|---|---|
| 5,352,199 | 10/1994 | Tower | 604/96 |
| 5,358,486 | 10/1994 | Saab | 604/96 |
| 5,364,356 | 11/1994 | Hofling | 604/96 |
| 5,364,358 | 11/1994 | Hewitt et al. | 604/99 |
| 5,380,282 | 1/1995 | Burns | 604/96 |
| 5,387,226 | 2/1995 | Miraki | 606/194 |
| 5,395,389 | 3/1995 | Patel | 606/194 |
| 5,411,016 | 5/1995 | Kume et al. | 128/6 |
| 5,413,557 | 5/1995 | Solar | 604/96 |
| 5,419,767 | 5/1995 | Eggers et al. | 604/114 |
| 5,470,313 | 11/1995 | Crocker et al. | 604/96 |
| 5,484,409 | 1/1996 | Atkinson et al. | 604/96 |
| 5,490,839 | 2/1996 | Wang et al. | 604/96 |
| 5,496,276 | 3/1996 | Wang et al. | 604/96 |
| 5,499,973 | 3/1996 | Saab | 604/96 |
| 5,507,731 | 4/1996 | Hernandez et al. | 604/264 |
| 5,512,051 | 4/1996 | Wang et al. | 604/96 |
| 5,514,093 | 5/1996 | Ellis et al. | 604/103 |
| 5,549,551 | 8/1996 | Peacock et al. | 606/194 X |
| 5,569,199 | 10/1996 | Solar | 604/96 |
| 5,591,194 | 1/1997 | Berthiaume | 606/192 |
| 5,599,307 | 2/1997 | Bacher et al. | 604/101 |
| 5,676,654 | 10/1997 | Ellis et al. | 604/103 |
| 5,843,092 | 12/1998 | Heller et al. | 606/194 X |

CATHETER HAVING A VARIABLE LENGTH BALLOON AND METHOD OF USING THE SAME

BACKGROUND OF THE INVENTION

The present invention relates to a catheter having a variable length balloon. More particularly, it relates to a balloon catheter having an adjustment device for allowing adjustment of an effective balloon inflation length.

Balloon catheters are widely used in a number of different applications. For example, a balloon catheter is highly useful for effectuating and/or finalizing placement of a stent within the urinary tract, a blood vessel, biliary duct, etc., to name but a few. Additionally, a balloon catheter can be used as part of an angioplasty procedure as an efficient and effective method for treating various types of vascular disease. In particular, angioplasty is widely used for opening a stenosis in a coronary artery, although it is also used for the treatment of a stenosis in other parts of the vascular system and other parts of the body.

In its most basic form, a balloon catheter generally includes a catheter shaft and an inflatable balloon. The catheter shaft defines an inflation lumen which extends to a distal end of the catheter shaft. The balloon, in turn, is attached to the distal end of the catheter shaft such that an interior of the balloon is in fluid communication with the inflation lumen. Balloon inflation is achieved by supplying pressurized fluid to the inflation lumen that in turn inflates the balloon.

Obviously, the above-described balloon catheter can and oftentimes does include a number of additional features. For example, the catheter shaft may include additional structure by which the balloon catheter can be directed to a particular site within the human body via a guidewire. In this regard, a number of different guidewire approaches are available, such as fixed wire, over-the-wire, and single operator exchange catheters. Additionally, the catheter shaft can be provided with other lumens for supplying specific therapeutic substances and/or instruments to the treatment site. Regardless of these additional features, the basic balloon catheter design includes a catheter shaft and a balloon fluidly connected to a distal end of the catheter shaft.

In one application of the above-described balloon catheter, a stent is placed over the balloon and delivered to a treatment site. Once properly in place, the balloon is inflated as previously described, causing the stent to expand and lodge against the walls of the particular duct being treated. This can be done as a follow-up to an angioplasty procedure. Alternatively, following stent placement, it may be necessary to re-expand or tack the stent against the duct walls. Once again, this procedure entails positioning the balloon, in a deflated state, within the stent and then inflating the balloon such that the balloon expands the stent.

With the above-described stent applications, balloon inflation length is highly important. With one accepted approach, the balloon inflation length is selected to be slightly longer than the length of a selected stent so that the entire stent, including its ends, is expanded by the balloon. Alternatively, other recognized methods include choosing a balloon inflation length equal to or slightly smaller than that of the stent. It is believed that this technique achieves adequate stent extension while eliminating the opportunity for undesirable contact between the balloon and the duct wall.

Regardless of the particular stent deployment technique, the standard balloon catheter design requires that a physician have on hand several catheters having different length balloons mounted thereon to accommodate different sized stents. Additionally, it may also require the physician to exchange catheters in the middle of a treatment process so that a catheter of proper balloon length can be utilized. Obviously, these factors can increase the cost of the particular procedure, along with the time required for treatment.

In another application of the above-described balloon catheter, the device is guided through the vascular system to a location near a stenosis. Using fluoroscopy, and assisted by a guidewire, a physician guides the balloon catheter the remaining distance through the vascular system until the balloon is positioned across the stenosis. The balloon is then inflated by supplying fluid under pressure through the inflation lumen in the catheter to the balloon. Inflation of the balloon causes widening of the lumen of the artery to reestablish acceptable blood flow through the artery.

Vascular occlusions to be treated by a balloon catheter can vary dramatically in size or length. With the variation in length of the occlusion, the area to be treated correspondingly varies in length. It is recognized as desirable to match the inflation length of the balloon as closely as possible to the length of the occlusion to be treated. This prevents expanding the balloon to a length otherwise resulting in pressing against a healthy artery wall. Similar to the drawbacks associated with stent application, the standard balloon catheter design requires, during a treatment, that a physician have on hand several catheters having different length balloons mounted thereon. It may also require the physician to exchange catheters in the middle of the treatment process so that a catheter of proper balloon length can be utilized.

The above problems can be overcome by incorporating a variable length balloon with a single catheter shaft which allows selecting the inflation length of the balloon at the time of or during treatment. Fogarty et al. (U.S. Pat. No. 4,564,014) and Saab (U.S. Pat. No. 5,246,421), the disclosures of which are incorporated herein by reference, disclose catheters incorporating a variable length balloon in a dilation catheter.

Fogarty et al. discloses a catheter including an elongated elastomeric tube closed at its distal end and extending the full length of the catheter. A telescopic sheath is received around the elastomeric tube, which has a distal primary section that is movable relative to the elastomeric tube and a proximal secondary section secured against movement relative to the elastomeric tube. A guidewire is disposed within and extends through the full length of the elastomeric tube with the guidewire having its distal end secured to the distal end of the tube, and its proximal end extending from the proximal end of the tube. The length of the balloon is thus adjusted by moving the distal primary section of the sheath while maintaining the position of the elastomeric tube and proximal secondary section of the sheath.

To facilitate movement of the primary sheath section relative to the elastomeric tube, Fogarty et al. discloses that the elastomeric tube may be stretched lengthwise to reduce its diametrical cross-section by extending the guidewire which is fixed to the distal end of the elastomeric tube. The fixing of the guidewire to the distal end of the elastomeric tube, although aiding in adjusting the size of the balloon, prevents use as an over-the-wire device. Further, the Fogarty et al. device requires that the telescopic sheath extend virtually the entire length of the elastomeric tube, increasing costs and opportunity for sheath movement. In other words, due to its length, the sheath can easily move upon inflation, creating unforeseen problems during use. Along these same lines, because the primary sheath is slidable relative to the secondary sheath, the primary sheath is free to move upon balloon inflation.

Saab also discloses an adjustable-length balloon dilation catheter apparatus incorporating an adjustable sheath which is externally manipulated to partially surround and contain the dilation balloon segment of the catheter while the catheter balloon segments are expanded during a treatment procedure. Saab discloses an adjustable sheath which is substantially co-axial with the catheter and substantially surrounds the catheter body, balloon and catheter tip. Saab discloses that the sheath may run the full length of the catheter or be provided at the distal end of a relatively stiff, controlled catheter, with the latter being co-axially mounted relative to the balloon catheter. Thus, similar to Fogarty et al., the Saab device includes a sheath extending along virtually the entire catheter shaft, thus giving rise to many of the problems described above. Additionally, while Saab briefly mentions that the sheath can be "fixed" by a clamping device or other conventional fastening techniques, no such disclosure or other teaching is provided. Thus, while Saab does provide one version of a variable length balloon catheter, this device provides no assurances that upon inflation, the balloon length will not unexpectedly change.

SUMMARY OF THE INVENTION

The present invention is a balloon catheter including an adjustment device for adjusting an effective balloon inflation length. The balloon catheter generally includes a balloon in fluid communication with a distal end of a catheter shaft having a distal portion. The adjustment device includes an outer sleeve and an attachment means. The outer sleeve is configured to be generally co-axially received over the distal portion of the catheter shaft. In this regard, at least a portion of the outer sleeve is configured to be slidable relative to the distal portion of the catheter shaft and the balloon such that a distal end of the outer sleeve can be positioned to restrict inflation of the balloon proximal the distal end of the outer sleeve. The attachment means is associated with the outer sleeve for selectively securing at least a portion of the outer sleeve to the distal portion of the catheter shaft such that positioning of the distal end of the outer sleeve at a desired location along the balloon length will not change upon inflation.

During use, a desired balloon inflation length is determined. This may entail reference to a particular stent length, stenosis size, etc. The outer sleeve is slid along the distal portion of the catheter shaft such that the distal end of the outer sleeve is positioned over the balloon at a location to restrict balloon inflation to an effective balloon inflation length equivalent to the desired length. The attachment means secures the outer sleeve in this position. The balloon catheter is then guided to the treatment site and the balloon inflated. The attachment means prevents movement of the outer sleeve following placement at the treatment site. However, the attachment means allows selective movement of the outer sleeve by a physician when the balloon catheter is not deployed such that the effective balloon inflation length can be changed.

In one preferred embodiment, the attachment means includes a rib and a locking sleeve. The rib is attached to and concentrically extends from a circumference of the distal portion of the catheter shaft proximal the balloon. The locking sleeve is generally co-axially received over the outer sleeve and is configured to selectively secure the outer sleeve to the rib. During use, the outer sleeve is maneuvered as previously described. Once properly positioned, the locking sleeve is positioned to engage the outer sleeve such that the outer sleeve is secured between the locking sleeve and the rib. In one preferred embodiment, a distal end of the outer sleeve is configured to allow at least partial inflation of the balloon both proximal and distal of the distal end such that the least partial inflation of the balloon assists in maintaining the position of the outer sleeve. Positioning of the outer sleeve can be changed by retracting the locking sleeve away from the rib, thereby freeing the outer sleeve to slide along the distal portion of the catheter shaft.

BRIEF DESCRIPTION OF THE DRAWINGS

In the drawings, in which like reference numerals indicate corresponding parts or elements of preferred embodiments of the present invention throughout the several views.

DETAILED DESCRIPTION OF THE INVENTION

Detailed embodiments of the present invention are disclosed herein. However, it is to be understood that the disclosed embodiments are merely exemplary of the present invention which may be embodied in various systems. Therefore, specific details disclosed herein are not to be interpreted as limiting, but rather as a basis for the claims and as a representative basis for teaching one of skill in the art to variously practice the invention.

Figure 1:
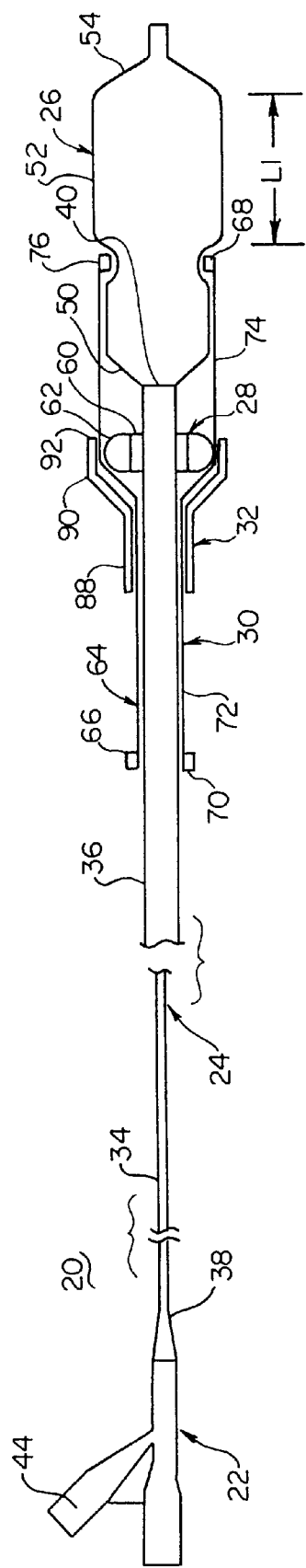
FIG. 1 is a partial, longitudinal cross-sectional view of a balloon catheter including an adjustment device in accordance with the present invention.

Now, referring to FIG. 1, a longitudinal cross-sectional view of a balloon catheter assembly 20 is shown. The balloon catheter assembly 20 includes a manifold 22, a catheter shaft 24, a balloon 26, a retention ring 28, a balloon adjustment sleeve 30, and a locking sleeve 32. The manifold 22 and the balloon 26 are fluidly connected at opposite ends of the catheter shaft 24. The retention ring 28 is disposed about an outer circumference of the catheter shaft 24. The balloon adjustment sleeve 30 is slidably disposed over the catheter shaft 24 and the balloon 26 in a generally co-axial fashion. Finally, the locking sleeve 32 is generally co-axially received over the balloon adjustment sleeve 30.

The catheter shaft 24 is of a standard construction and includes a tubular body defined by a proximal portion 34 and a distal portion 36. For ease of illustration, the distal portion 36 is enlarged in FIG. 1. The proximal portion terminates in a proximal end 38. Similarly, the distal portion 36 terminates at a distal end 40. Finally, the catheter shaft 24 includes an inflation lumen (not shown) extending from the proximal end 38 to the distal end 40. Notably, the catheter shaft 24 may also define additional lumens, such as a guidewire lumen (not shown). Thus, the catheter shaft can be an over-the-wire, fixed wire, single operator exchange, stent delivery, etc., catheter.

The catheter shaft is preferably made from standard catheter material such as nylon. Alternatively, other materials such as polyethylene, polyurethane, polyethylene terephthalate (PET), polyetheretherketone (PEEK), polyether block amide (PEBA), nylon, PEEK braid, SS hypotube, etc., may also be useful.

The manifold 22 is of a standard construction and is attached to the proximal end 38 of the catheter shaft 24. In this regard, the manifold 22 includes an inflation port 44 in fluid communication with the inflation lumen (not shown) of the catheter shaft 24. In a preferred embodiment, the manifold 22 is constructed from a polycarbonate material. Alternatively, other rigid materials may also be useful.

The balloon 26 includes a proximal end 50, an intermediate portion 52 and a distal end 54. An inside diameter surface of the proximal end 50 is configured to be secured to an outside diameter surface of the distal end 40 of the catheter shaft 24 such that an interior of the balloon 26 is in fluid communication with the inflation lumen (not shown) of the catheter shaft 24. A preferred balloon material is PEBAX. Alternatively, other materials commonly used for construction of a balloon for use with a balloon catheter, such as polyethylene terephthalate (PET) ARNITEL, may also be useful. An adhesive may be utilized to secure the proximal end 50 of the balloon 26 to the distal end 40 of the catheter shaft 24.

The retention ring 28 is configured to extend in a concentric fashion from an outer circumference of the distal portion 36 of the catheter shaft 24. In a preferred embodiment, the retention ring 28 includes an interior portion 60 and an exterior portion 62. The interior portion 60 is configured to be secured to the distal portion 36 of the catheter shaft 24 and is preferably made of nylon, such as VESTAMID from Huls America. Also, stainless steel could be used. Alternatively, other rigid materials may also be useful. The exterior portion 62 is fixed to the interior portion 60 as shown in FIG. 1 and preferably forms a circular outer surface. In a preferred embodiment, the exterior portion 62 is made of an elastic material such as urethane or latex and is fixed to the interior portion 60 by an adhesive.

While the retention ring 28 has been preferably described as being a ring, other shapes may also be employed. For example, the retention ring 28 may instead be a rib extending from the distal portion 36 of the catheter shaft 24 only partially about a circumference of the catheter shaft 24.

The balloon adjustment sleeve 30 includes an outer sleeve 64, a stop collar 66 and a marker band 68. The outer sleeve 64 is defined by a proximal end 70, a proximal portion 72, a distal portion 74 and a distal end 76. The stop collar 66 is disposed at the proximal end 70 of the outer sleeve 64, whereas the marker band 68 is disposed at the distal end 76.

The outer sleeve 64 is preferably tubular in shape, sized to be generally co-axially received over the distal portion 36 of the catheter shaft 24. Thus, in one preferred embodiment, the outer sleeve 64 has a diameter equal to or slightly larger than an outer diameter of the catheter shaft 24. Further, in one preferred embodiment, the distal portion 74 of the outer sleeve 64 has a diameter slightly greater than a diameter of the proximal portion 72 of the outer sleeve 64. In this regard, the distal portion 74 of the outer sleeve 64 has a diameter approximating an outer diameter of the retention ring 28.

The outer sleeve 64 is preferably made of a semi-flexible material such as polyethylene teraphthalate (PET). Alternatively, other similar materials, such as NC PET, polyethylene, polypropylene, PEBAX, CRISTAMID, PEEK, etc., may also be useful.

The stop collar 66 is preferably a ring having an inner diameter less than an outer diameter of the retention ring 28. The stop collar 66 is preferably made of a rigid material such as VESTAMID. Alternatively, other rigid materials such as stainless steel may also be useful. The stop collar 66 is preferably secured to the proximal end 70 of the outer sleeve 64 by an adhesive.

The marker band 68 is preferably a ring-shaped body having an inner diameter slightly larger than the diameter of the balloon 26 when folded. In a preferred embodiment, the marker band 68 is constructed of a material visible utilizing fluoroscopy techniques. This configuration allows determination of balloon location during treatment. Alternatively, or in addition to the marker band 68, markings may be included on an outside surface of the catheter shaft 24 in the area of the distal end 40, or on the distal portion 36 of the catheter shaft 24, or on the balloon 26. Even further, the outer sleeve 64 can include a radiopaque loading, such as tungsten or gold. In addition to providing fluoroscopic identification, the marker band 68 also serves as a reinforcement to the distal end 76 of the outer sleeve 64.

The marker band 68 further serves to prevent the outer sleeve 64 from sliding when the balloon 26 is inflated due to an inflated portion of the balloon both distal and proximal of the marker band 68. In this regard, the marker band 68 is preferably configured as a relatively rigid shoulder to facilitate inflation restriction of the balloon 26 as described in greater detail below. Because the marker band 68 is in contact with the balloon 26 upon inflation, the marker band 68 preferably has a rounded interior surface. Alternatively, the marker band 68 may assume a conical shape.

The locking sleeve 32 is a generally tubular body including a proximal portion 88 and a distal portion 90. The proximal portion 88 is preferably configured to have an inner diameter less than an outer diameter of the retention ring 28. The distal portion 90, as shown in FIG. 1, preferably expands in diameter from the proximal portion 88 to a distal end 92. In this regard, the distal portion 90 preferably assumes a conical or funnel shape. The distal end 92 of the distal portion 90 preferably has a diameter approximating the outer diameter of the retention ring 28. Alternatively, the distal portion 90 need not be curved and may instead have a diameter slightly smaller than that of the retention ring 28.

In a preferred embodiment, the locking sleeve 32 is made of a rigid material such as a VESTAMID. Alternatively, other rigid, surgically-safe materials such as polypropylene may also be useful. Regardless of exact form, the locking sleeve 32 is configured to slide over the balloon adjustment sleeve 30 and engage the retention ring 28.

The above-described balloon catheter assembly 20 is constructed basically as follows. The retention ring 28 is secured to an exterior of the catheter shaft 24 along the distal portion 36 near the distal end 40. The balloon 26 is adhered to the distal end 40 of the catheter shaft 24 in fluid communication with the inflation lumen (not shown). The balloon adjustment sleeve 30 is slid in a co-axial fashion over the distal portion 36 of the catheter shaft 24 such that the distal end 76 of the outer sleeve 64 is distal the retention ring 28. The locking sleeve 32 is slid in a co-axial fashion over the balloon adjustment sleeve 30. Finally, the manifold 22 is secured to the proximal end 38 of the catheter shaft 24 such that the inflation port 44 is in fluid communication with the inflation lumen of the catheter shaft 24.

As previously described, the stop collar 66 preferably has a diameter less than an outer diameter of the retention ring 28. Thus, the stop collar 66 prevents the balloon adjustment sleeve 30 from sliding off of or otherwise disengaging from the distal end 40 of the catheter shaft 24.

The above-described balloon catheter assembly 20 can be used in any of a number of applications requiring use of a balloon catheter. A desired balloon inflation length is first determined. For example, with stent delivery or tacking, a length of the stent (not shown) is ascertained. The balloon adjustment sleeve 30 is maneuvered relative to the distal portion 36 of the catheter shaft 24 and the balloon 26 to provide a balloon inflation length equivalent to the desired balloon inflation length. In this regard, the locking sleeve 32 is retracted from engagement with the retention ring 28, toward the proximal end 38 of the catheter shaft 24. The balloon adjustment sleeve 30 is then free to slide over the distal portion 36 of the catheter shaft 24 and the balloon 26. To facilitate maneuvering of the balloon adjustment sleeve 30 relative to the balloon 26, the balloon 26 is preferably in a deflated state. The balloon adjustment sleeve 30 is slid to a position whereby the distal end 76 of the outer sleeve 64 encircles the balloon 26 at a position providing the effective balloon inflation length (designated as the length L1 in FIG. 1).

With the balloon adjustment sleeve 30 properly positioned, the locking sleeve 32 is slid over the outer sleeve 64, toward the distal end 40 of the catheter shaft 24. As previously described, the distal portion 90 of the locking sleeve 32 has a conical shape, reducing in diameter from the distal end 92 to the proximal portion 88. Thus, as the locking sleeve 32 moves toward the distal end 40 of the catheter shaft 24, the distal portion 90 frictionally secures the outer sleeve 64 to the retention ring 28. In other words, the outer sleeve 64 is locked or pinched between the locking sleeve 32 and the retention ring 28. Notably, the exterior portion 62 of the retention ring 28 is preferably made of an elastic material to enhance frictional interaction between the outer sleeve 64 and the retention ring 28. In this secure position, the distal end 76 of the outer sleeve 64 is fixed relative to the balloon 26.

Once the balloon adjustment sleeve 30 is secured at a desired position, the balloon catheter assembly 20 is ready for deployment. For example, where the balloon catheter assembly 20 is for stent delivery, a stent (not shown) is crimped over the effective balloon inflation length L1 of the balloon 26. The balloon catheter assembly 20 is then guided to the treatment site. The balloon 26 is inflated via fluid supplied from the manifold 22 through the inflation lumen (not shown). Upon inflation, the distal end 76 of the outer sleeve 64 restricts inflation of the balloon 26 proximal the distal end 76. Notably, the distal portion 74 in conjunction with the marker band 68 is preferably configured to maintain its shape to a pressure of at least 15–18 atmosphere.

In the preferred embodiment, as previously described, the distal portion 74 of the outer sleeve 64 has an inner diameter slightly larger than that of the marker band 68 of the outer sleeve 64. Thus, the distal portion 74 allows the balloon 26 to inflate slightly proximal the distal end 76 of the outer sleeve 64. This slight inflation assists in securing the balloon adjustment sleeve 30 in place as the balloon 26 inflates both distal and proximal of the marker band 68. In other words, inflation of the balloon along the effective balloon inflation length L1 applies a force against the distal end 76 of the outer sleeve 64 at the marker band 68. The slight inflation proximal the distal end 76 of the outer sleeve 64 at least partially counteracts this force to prevent any movement of the balloon adjustment sleeve 30. With this preferred construction, the marker band 68 functions as an annular shoulder, configured to allow at least partial inflation of the balloon 26 both proximal and distal of the marker band 68. This at least partial inflation holds the outer sleeve 64 in position to maintain the effective balloon inflation length L1.

A similar procedure can be employed for other balloon catheter assembly 20 applications. For example, when the balloon catheter assembly 20 is to be used to expand or tack a previously-applied stent, a desired balloon inflation length is determined. The effective balloon inflation length L1 is then adjusted to accommodate this desired length by maneuvering and securing the balloon adjustment sleeve 30 as previously described. In other words, the balloon catheter assembly 20 allows a physician to adjust the effective balloon inflation length L1 to a length of the stent (not shown). Similarly, where the balloon catheter assembly 20 is to be used to enlarge a duct obstruction, such as in a blood vessel or urinary tract, the length of the obstruction is determined. The balloon adjustment sleeve 30 is then maneuvered and secured by the locking ring 32 to the retention ring 28 such that the distal end 76 of the outer sleeve 64 is positioned to provide an appropriate, effective balloon inflation length L1 matching the length of the obstruction.

The above-described balloon catheter assembly 20 provides a variable length balloon catheter configured to allow physician adjustment of the outer sleeve 64 along the distal portion 36 of the catheter shaft 24 to alter the effective balloon inflation length. The outer sleeve 64 is relatively short and need not extend to the proximal portion 34 of the catheter shaft 24. It should be recognized, however, that the preferred embodiment shown in FIG. 1 is only one embodiment of the present invention. In other words, other embodiments are envisioned within the scope of the present invention whereby an adjustment device, including an outer sleeve 64 and an attachment means (such as the retention ring 28 and the locking sleeve 32), provides an adjustable balloon inflation length.

Figure 2B:
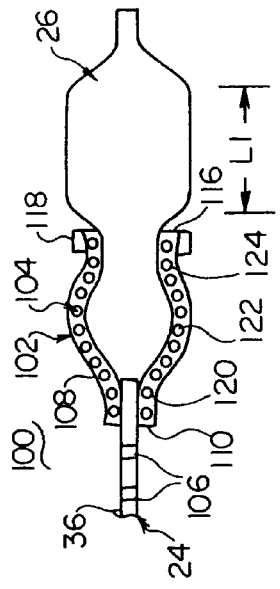
FIGS. 2A and 2B are partial, longitudinal cross-sectional views of the distal portion of a balloon catheter including an alternative embodiment of an adjustment device in accordance with the present invention.
Figure 2A:
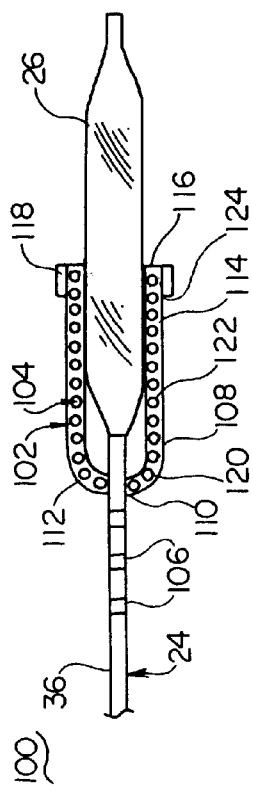

For example, FIGS. 2A and 2B provide an alternative embodiment of a balloon catheter assembly 100. Notably, because all necessary components are disposed on the distal portion 36 of the catheter shaft 24, only the distal portion 36 need be shown. With reference to FIG. 2A, the balloon catheter assembly 100 includes the catheter shaft 24 and the balloon 26. The balloon 26 is fluidly connected to the inflation lumen (not shown) of the catheter shaft 24 at the distal end 40. The balloon catheter assembly 100 further includes a balloon adjustment sleeve 102 generally co-axially received over the distal portion 36 of the catheter shaft 24 and an elastic coil 104 encompassed by the balloon adjustment sleeve 102.

The catheter shaft 24 is identical to that previously described. Thus, the catheter shaft 24 can assume a number of different forms such as an over-the-wire, fixed wire, single operator exchange, stent delivery, etc., catheter. Additionally, however, the catheter shaft 24 includes markings 106 disposed along the distal portion 36 proximate the distal end 40. As described in greater detail below, the markings 106 are positioned to provide an indication of effective balloon inflation length.

The balloon adjustment sleeve 102 includes an outer sleeve 108, defined by a proximal end 110, a proximal portion 112, a distal portion 114 and a distal end 116, and a marker band 118 similar to that previously described. The outer sleeve 108 is preferably tubular in shape and is made of a material similar to the outer sleeve 64 (FIG. 1) previously described. The proximal end 110 of the outer sleeve 108 has an inner diameter approximating an outer diameter of the catheter shaft 24. As described in greater detail below, the outer sleeve 108 is preferably configured to encase the elastic coil 104.

The elastic coil 104 includes a proximal portion 120, an intermediate portion 122 and a distal portion 124. In this regard, while the elastic coil 104 is preferably flexible, the proximal portion 120 and the distal portion 124 are preferably configured to be more rigid than the intermediate portion 122. For example, spacing between concentric rings of the elastic coil 104 can be more compact at the proximal portion 120 and the distal portion 124 of the elastic coil 104 than at the intermediate portion 122. The elastic coil 104 is preferably sized to correspond to the diameter variations of the outer sleeve 108 portions. In this regard, the proximal portion 120 of the elastic coil 104 preferably has an inner diameter approximating that of the distal portion 36 of the catheter shaft 24. While the elastic coil 104 has been preferably described as being a coil, other devices may also be useful. For example, the elastic coil 104 may be a spring or a braid.

The outer sleeve 108 is preferably formed about the elastic coil 104 through a molding process. Alternatively, other accepted methods of manufacturing may also be useful so that the elastic coil 106 is encased within the outer sleeve 108. The marker band 118 is secured to the distal end 116 of the outer sleeve 108 by an adhesive.

The balloon catheter assembly 100 is used in a manner highly similar to the balloon catheter assembly 20 (FIG. 1) previously described. In this regard, the balloon 26 is adhered to the distal end 40 of the catheter shaft 24. The balloon adjustment sleeve 102, including the elastic coil 104, is co-axially received over the distal portion 36 of the catheter shaft 24.

A desired balloon inflation length is determined, as previously described. The balloon adjustment sleeve 102 is slid along the distal portion 36 of the catheter shaft 24 to position the distal end 116 of the outer sleeve 108 along the balloon 26 to effectuate an effective balloon inflation length L1 equivalent to the desired balloon inflation length. In this regard, the markings 106 along the catheter shaft 24 assist the physician in achieving proper positioning of the balloon adjustment sleeve 102. The markings 106 are made at increments of approximately one millimeter, as measured from the distal end 40 of the catheter shaft 24, and relate to a length of the balloon adjustment sleeve 102 and the balloon 26. In other words, because a length of the balloon adjustment sleeve 102 and the balloon 26 are known, the markings 106 can be disposed and identified along the distal portion 36 of the catheter shaft 24 such that a physician can align the proximal end 110 of the outer sleeve 108 at a particular one of the markings 106 with the result being a known, effective balloon inflation length L1. To assist in sliding the balloon adjustment sleeve 102 over the catheter shaft 24, the balloon 26 is preferably deflated, at low pressure, or under vacuum.

With the balloon adjustment sleeve 102 properly positioned, the balloon catheter assembly 100 is ready for use. Once again, a stent can be placed over the balloon 26 distal the distal end 116 of the outer sleeve 108 and the entire assembly 100 guided to a treatment site. Alternatively, the balloon catheter assembly 100 can be positioned at the treatment site for tacking a previously-applied stent or expansion of an obstruction. Regardless of the specific application, the balloon adjustment sleeve 102 restricts inflation of the balloon 26 proximal the distal end 116 of the outer sleeve 108.

As shown in FIG. 2B, the balloon adjustment sleeve 102 and the elastic coil 104 allow for slight inflation of the balloon 26 proximal the distal end 116 of the outer sleeve 108. In this regard, the intermediate portion 122 of the elastic coil 104 allows for a slight bulge in response to inflation of the balloon 26. Once again, the proximal portion 120 and the distal portion 124 of the elastic coil 104 are more compact such that minimal expansion of the elastic coil 104, and thus of the outer sleeve 108, occurs upon inflation of the balloon 26. However, because the intermediate portion 122 of the elastic coil 124 is slightly more elastic, a portion of the balloon 26 proximal the distal end 116 of the outer sleeve 108 inflates slightly. This bulge in the intermediate portion 122 of the elastic coil 104, and thus in the outer sleeve 108, acts to secure the balloon adjustment sleeve 102 at the desired position. The distal end 116 of the outer sleeve 108 is locked between the balloon 26 proximal and distal the distal end 116 of the outer sleeve 108 upon inflation. Effectively then, the distal end 116 of the outer sleeve 108 is preferably configured to serve as an annular shoulder, ensuring consistent positioning upon inflation of the balloon 26.

Notably, the proximal end 110 of the outer sleeve 108 and of the elastic coil 104 has a diameter approximating that of the catheter shaft 24. Thus, due to this reduced diameter and rigidity of the proximal portion 120 of the elastic coil 104, the balloon adjustment sleeve 102, including the elastic coil 104, are prevented from falling off of or otherwise disengaging from the distal end 40 of the catheter shaft 24.

Similar to the embodiment shown in FIG. 1, the embodiment provided in FIGS. 2A and 2B can be generally described as including the outer sleeve 108 having the distal end 116 configured to restrict inflation of the balloon 26 and an attachment means (i.e., the elastic coil 104) configured to secure the outer sleeve 108 relative to the distal portion 36 of the catheter shaft 24.

Figure 3:
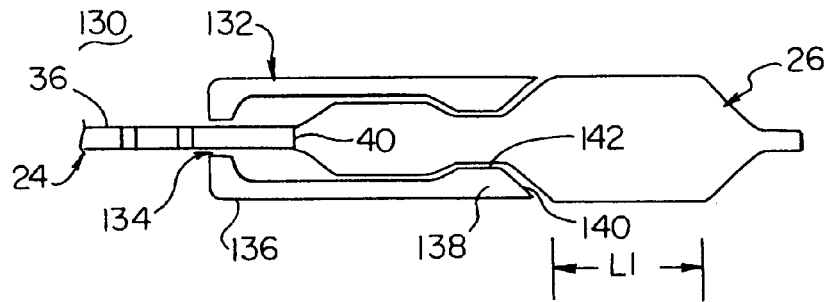
FIG. 3 is a partial, longitudinal cross-sectional view of the distal portion of a balloon catheter including an alternative embodiment of an adjustment device in accordance with the present invention.

Another embodiment of a balloon catheter assembly 130 is provided in FIG. 3. Similar to previous embodiments, the balloon catheter assembly 130 includes the catheter shaft 24, having the distal portion 36, and the balloon 26 fluidly connected to the distal end 40 of the catheter shaft 24. The balloon catheter assembly 130 further includes a balloon adjustment sleeve 132 having a proximal end 134, a proximal portion 136, a distal portion 138 and a distal end 140.

The balloon adjustment sleeve 132 is generally a tubular body configured to be co-axially received over the distal portion 136 of the catheter shaft 24 and the balloon 26. In this regard, the proximal end 124 of the balloon adjustment sleeve 132 has an inner diameter approximating an outer diameter of the catheter shaft 24. Further, the proximal portion 36 of the balloon adjustment sleeve 132 has an inner diameter slightly larger than an outer diameter of the catheter shaft 24. Finally, the distal portion 138 of the balloon adjustment sleeve 132 is tapered on opposite ends thereof and forms a balloon receiving surface 142. In other words, the distal portion 138 of the balloon adjustment sleeve 132 is configured to taper inwardly from the proximal portion 136 to a reduced diameter at the balloon receiving surface 142. Conversely, the distal portion 138 of the balloon adjustment sleeve 132 is configured to expand from the balloon receiving surface 142 to the distal end 140 as shown in FIG. 3. As described in greater detail below, the preferred construction of the distal portion 138 of the balloon adjustment sleeve 132 allows complete inflation of the balloon 26 distal the distal end 140 and slight inflation of the balloon 26 proximal the distal end 140 of the balloon adjustment sleeve 132.

In a preferred embodiment, the balloon adjustment sleeve 132 is made of a rigid, surgically-safe polymer such as CRISTAMID®. Alternatively, the balloon adjustment sleeve 132 can be made of a surgically-safe metallic material, such as stainless steel.

The balloon catheter assembly 130 is used in a manner highly similar to previous embodiments. In this regard, the balloon adjustment sleeve 132 is able to co-axially slide over the distal portion 36 of the catheter shaft 24 and the balloon 26. After determining a desired balloon inflation length, the balloon adjustment sleeve 132 is positioned along the distal portion 36 of the catheter shaft 24 such that the distal end 140 provides an effective balloon inflation length L1 equivalent to the desired balloon inflation length. In a preferred embodiment, the balloon 26 is deflated, at a low pressure, or under vacuum to facilitate placement of the balloon adjustment sleeve 132.

Once the balloon adjustment sleeve 132 is properly positioned relative to the balloon 26, the balloon catheter assembly 130 is ready for deployment, such as, for example, to deliver a stent or expand an obstruction. Once properly positioned at the treatment site, the balloon 26 is inflated. As shown in FIG. 3, the balloon 26 is allowed to fully inflate distal the distal end 140 of the balloon adjustment sleeve 132. Further, due to the enlarged inner diameter of the proximal portion 136 of the balloon adjustment sleeve 132, slight inflation of the balloon 26 proximal the distal portion 138 is allowed. This slight inflation serves to secure the balloon adjustment sleeve 132 relative to the distal portion 36 of the catheter shaft 24 and the balloon 26. In other words, the balloon receiving surface 142 restricts balloon inflation. However, due to the tapered nature of the distal portion 138, the balloon 26 will inflate at opposite sides. The balloon 26, upon inflation, applies a force on the opposing tapered walls of the distal portion 138, thus preventing movement of the balloon adjustment sleeve 132. With this configuration, then, the tapered configuration of the distal portion 138 serves as an attachment means for selectively securing the balloon adjustment sleeve 132.

Figure 4A:
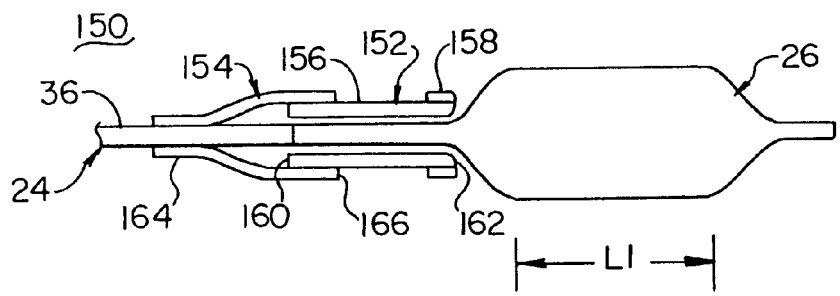
FIGS. 4A and 4B are partial, longitudinal cross-sectional views of the distal portion of a balloon catheter including an alternative embodiment of an adjustment device in accordance with the present invention.
Figure 4B:
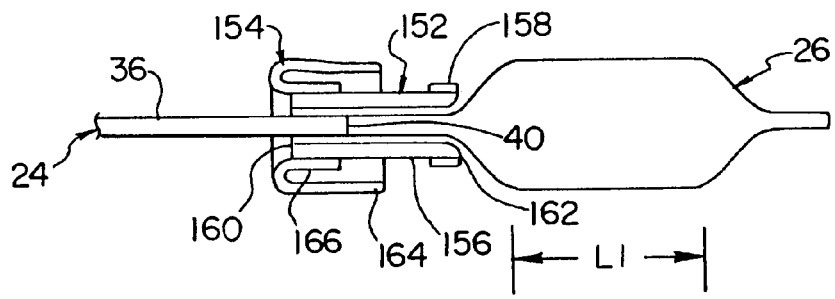

Yet another alternative embodiment of a balloon catheter assembly 150 is shown in FIGS. 4A and 4B. Similar to previous embodiments, the balloon catheter assembly 150 includes the catheter shaft 24, having the distal portion 36, and the balloon 26 fluidly connected to the distal end 40. Additionally, the balloon catheter assembly 150 includes a balloon adjustment sleeve 152 and a locking sleeve 154. The balloon adjustment sleeve 152 is generally co-axially received over the distal portion 36 of the catheter shaft 24. Further, as described in greater detail below, the locking sleeve 154 extends from the balloon adjustment sleeve 152 and is maneuverable between a locked position (FIG. 4A) and a released position (FIG. 4B).

The balloon adjustment sleeve 152 is similar to those previously described and includes an outer sleeve 156 and a marker band 158. The outer sleeve 156 is similar to the outer sleeve 64 previously described with reference to FIG. 1 and is defined by a proximal end 160 and a distal end 162. The outer sleeve 156 is preferably made of a flexible material such as polyethylene teraphthalate. Similarly, the marker band 158 is identical to that previously described and is preferably adhered to the distal end 162 of the outer sleeve 156 by an adhesive.

The locking sleeve 154 is a tubular body and is defined by a proximal end 164 and a distal end 166. The proximal end 164 of the locking sleeve 154 is configured to have an inner diameter less than an outer diameter of the distal portion 36 of the catheter shaft 24 when the proximal end 164 is in the locked position (FIG. 4A). The locking sleeve 154 is preferably made of an elastic material such as urethane. Alternatively, other materials, such as silicon or latex, may also be useful. Regardless of exact material, the locking sleeve 154 is configured to be maneuverable from the locked position (FIG. 4A) to the released position (FIG. 4B). The distal end 166 of the locking sleeve 154 is secured to the proximal end 160 of the outer sleeve 156 by an adhesive.

The balloon catheter assembly 150 functions in a manner highly similar to previous embodiments. In this regard, a desired balloon inflation length is first determined. The balloon adjustment sleeve 152 is then co-axially slid over the distal portion 36 of the catheter shaft 24 and a portion of the balloon 26 to provide for an effective balloon inflation length L1 equivalent to the desired balloon inflation length as defined by the distal end 162 of the outer sleeve 156. To allow movement of the balloon adjustment sleeve 152, the locking sleeve 154 is positioned in the released positioned shown in FIG. 4B. Due to the preferred elastic nature of the locking sleeve 154, the proximal end 164 of the locking sleeve 154 can be rolled or otherwise maneuvered over the outer sleeve 156 such that the locking sleeve 154 does not contact the catheter shaft 24. In this position, the balloon attachment sleeve 152 is free to slide back and forth along the distal portion 36 of the catheter shaft 24 and the balloon 26.

Once the distal end 162 of the outer sleeve 156 is properly positioned along the balloon 26 to provide for the desired balloon inflation length L1, the locking sleeve 154 is maneuvered into the engaged position (FIG. 4A). More particularly, the proximal end 164 of the locking sleeve 154 is rolled away from the outer sleeve 156 such that the proximal end 164 of the locking sleeve 154 contacts the catheter shaft 24. The proximal end 164 of the locking sleeve 154 preferably has an inner diameter slightly smaller than an outer diameter of the distal portion 36 of the catheter shaft 24. Thus, the proximal end 164 of the locking sleeve 154 grips the distal portion 36 of the catheter shaft 24, thereby securing the distal end 162 of the outer sleeve 156 relative to the balloon 26 and the distal portion 36 of the catheter shaft 24. Upon inflation of the balloon 26, the outer sleeve 156 is relatively rigid so as to restrict balloon inflation proximal the distal end 162 of the outer sleeve 156.

Figure 5A:
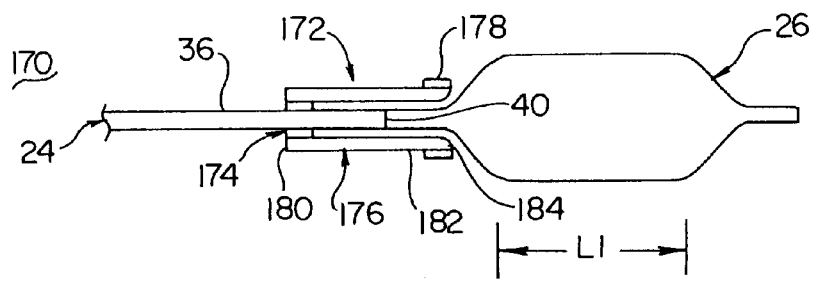
FIG. 5A is a partial, longitudinal cross-sectional view of the distal portion of a balloon catheter including an alternative embodiment of an adjustment device in accordance with the present invention.

Yet another alternative embodiment of a balloon catheter assembly 170 is shown in FIG. 5. Similar to previous embodiments, the balloon catheter assembly 170 includes the catheter shaft 24, having the distal portion 36, and the balloon 26 fluidly connected to the distal end 40 of the catheter shaft 24. Further, the balloon catheter assembly 170 includes a balloon adjustment sleeve 172 and a gripping body 174 secured to the balloon adjustment sleeve 172.

The balloon adjustment sleeve 172 is similar to the balloon adjustment sleeve 152 (FIGS. 4A and 4B) previously described. Thus, the balloon adjustment sleeve 172 includes an outer sleeve 176 and a marker band 178. The outer sleeve 176 is a generally tubular body sized to be co-axially received over the distal portion 36 of the catheter shaft 24 and includes a proximal end 180, an intermediate portion 182 and a distal end 184. The outer sleeve 176 is preferably made of a surgically-safe polymer, such as PET, and is relatively rigid along the intermediate portion 182. The marker band 178, which is identical to that previously described, is adhered to the distal end 184 of the outer sleeve 176.

The gripping body 174 is preferably a ring-shaped device having an inner diameter slightly larger than an outer diameter of the distal portion 36 of the catheter shaft 24. The gripping body 174 is preferably made of a flexible material having a shape retention characteristic. Thus, the gripping body 174 is preferably made of a flexible polymer or a flexible metal, such as nitinol. As described in greater detail below, with this configuration, the gripping body 174 can be forced from a circular shape to an oval shape, and vice-versa. The gripping body 174 is adhered to an interior surface of the proximal end 180 of the outer sleeve 176 by an adhesive.

The balloon catheter assembly 170 functions in a manner highly similar to previous embodiments. Thus, the balloon adjustment sleeve 172 and the attached gripping body 174 are co-axially received over the distal portion 36 of the catheter shaft 24 and a portion of the balloon 26. Upon determination of a desired balloon inflation length, the balloon adjustment sleeve 172 is maneuvered such that the distal end 184 is positioned along the balloon 26 to provide an effective balloon inflation length L1 equivalent to the desired balloon inflation length. To facilitate sliding of the balloon adjustment sleeve 172, the gripping body 174 is oriented to have an approximately circular shape, as shown in FIG. 5C. With the circular shape, the gripping body 174 has an inner diameter slightly larger than an outer diameter of the distal portion 36 of the catheter shaft 24. Thus, the gripping body 174 does not impede movement of the balloon adjustment sleeve 172 to the desired position relative to the distal portion 36 of the catheter shaft 24 and the balloon 26. Once the distal end 184 of the outer sleeve 176 is properly positioned about the balloon 26, the gripping body 174 is secured to the catheter shaft 24.

Figure 5B:
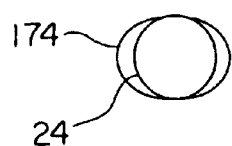
FIGS. 5B and 5C are cross-sectional views of a portion of the balloon catheter of FIG. 5A, including a gripping body and catheter shaft.
Figure 5C:
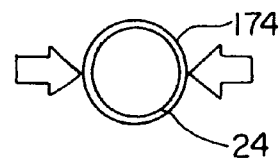

More particularly, as shown in FIG. 5B, a physician squeezes or otherwise applies forces at opposite sides of the gripping body 174. Following application of these opposing forces, the gripping body 174 assumes an oval shape having a minor diameter smaller than an outer diameter of the distal portion 36 of the catheter shaft 24. Thus, when oval-shaped, the gripping body 174 secures the balloon adjustment sleeve 172 to the distal portion 36 of the catheter shaft 24 such that upon inflation of the balloon 26, the balloon adjustment sleeve 172 will not move. The balloon adjustment sleeve 172 can subsequently be moved by squeezing or otherwise forcing the gripping body 174 to the approximately circular shape (FIG. 5C). Generally speaking, then, the gripping body 174 serves as an attachment means for selectively securing a portion of the balloon adjustment sleeve 172 to the distal portion 36 of the catheter shaft 24.

Figure 6:
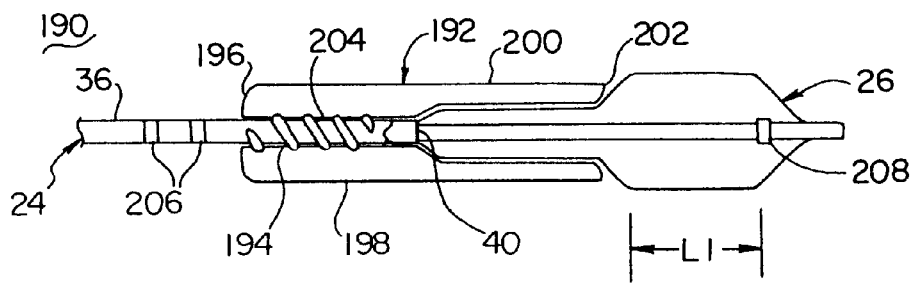
FIG. 6 is a partial, longitudinal cross-sectional view of the distal portion of a balloon catheter including an alternative embodiment of an adjustment device in accordance with the present invention.

Yet another alternative embodiment of a balloon catheter assembly 190 is shown in FIG. 6. Similar to previous embodiments, the balloon catheter assembly 190 includes the catheter shaft 24, having the distal portion 36, and the balloon 26 fluidly connected to the distal end 40 of the catheter shaft 24. Additionally, the balloon catheter assembly 190 includes a balloon adjustment sleeve 192 and threads 194 disposed along an outer circumference of the distal portion 36 of the catheter shaft 24. As described in greater detail below, the threads 194 are sized to selectively secure the balloon adjustment sleeve 192 to the distal portion 36 of the catheter shaft 24.

The balloon adjustment sleeve 192 is a generally tubular body defined by a proximal end 196, a proximal portion 198, a distal portion 200 and a distal end 202. The proximal portion 198 includes a thread receiving interior surface 204. In a preferred embodiment, the balloon adjustment sleeve 192 is formed as a singular body. In this regard, the balloon adjustment sleeve 192 is made of a relatively rigid, surgically-safe material such as nylon. Alternatively, other materials, such as polyethylene, CRISTAMID®, stainless steel, nitinol, etc., may also be useful.

The threads 194 are preferably disposed about an outer circumference of the distal portion 36 of the catheter shaft 24. In a preferred embodiment, the threads 194 are made of a relatively rigid material, such as stainless steel. Alternatively, other materials, such as nylon, polyethylene, nitinol or polyethylene teraphthalate may also be useful. Regardless of exact form, the threads 194 can be secured to the distal portion 36 of the catheter shaft 24 by an adhesive. Alternatively, the threads 194 can be formed during extrusion of the catheter shaft 24 such that the threads 194 are integral with the distal portion 36 of the catheter shaft 24.

The balloon catheter assembly 190 functions in a manner highly similar to previous embodiments. In this regard, the balloon adjustment sleeve 192 is co-axially received over the distal portion 36 of the catheter shaft 24 such that the thread receiving interior surface 204 of the balloon adjustment sleeve 192 threadably engages the threads 194. After determining a desired balloon inflation length, the balloon adjustment sleeve 192 is maneuvered relative to the distal portion 36 of the catheter shaft 24 and the balloon 26 such that the distal end 202 of the balloon adjustment sleeve 192 is positioned to establish an effective balloon inflation length L1 equivalent to the desired balloon inflation length. Markings 206 may be provided along the distal portion 36 of the catheter shaft 24 to assist in positioning of the balloon adjustment sleeve 192.

Once the balloon adjustment sleeve 192 is properly positioned, the balloon catheter assembly 190 is ready for use. Upon inflation of the balloon 26, interaction of the thread receiving interior surface 204 of the balloon adjustment sleeve 192 and the threads 194 secures the balloon adjustment sleeve 192 to the distal portion 36 of the catheter shaft 24, and thus serve as an attachment means. Positioning of the balloon adjustment sleeve 192 can subsequently be changed by rotating the adjustment sleeve 192 about the threads 194.

Figure 7:
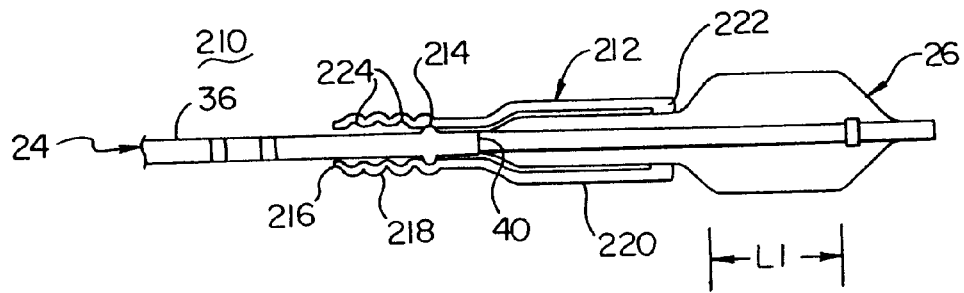
FIG. 7 is a partial, longitudinal cross-sectional view of the distal portion of a balloon catheter including an alternative embodiment of an adjustment device in accordance with the present invention.

Yet another alternative embodiment of a balloon catheter assembly 210 is shown in FIG. 7. Similar to previous embodiments, the balloon catheter assembly 210 includes the catheter shaft 24, having the distal portion 36, and the balloon 26 fluidly connected to the distal end 40 of the catheter shaft 24. Additionally, the balloon catheter assembly 210 includes a balloon adjustment sleeve 212, co-axially received over the distal portion 36 of the catheter shaft 24, and a friction ring attached to the distal portion 36 of the catheter shaft 24.

The balloon adjustment sleeve 212 is a singular body constructed from a material similar to previous embodiments and includes a proximal end 216, a proximal portion 218, a distal portion 220 and a distal end 222. The proximal end 216 is preferably sized to have an inner diameter approximating an outer diameter of the distal portion 36 of the catheter shaft 24. The proximal portion 218 is flexible and is configured to assume an accordion shape, defining a series of slots 224. The distal portion 220 of the balloon adjustment sleeve 212 is configured to have a diameter slightly greater than an outer diameter of the distal portion 36 of the catheter shaft 24. Finally, the distal end 222 of the balloon adjustment sleeve 212 is configured to taper to a diameter sized to restrict inflation of the balloon 26. In one preferred embodiment, the proximal end 216 of the balloon adjustment sleeve 212 is secured to the distal portion 36 of the catheter shaft 24 by an adhesive.

The friction ring 214 is preferably a ring sized to extend from an outer circumference of the distal portion 36 of the catheter shaft 24. The friction ring 214 is preferably made of a rigid material, such as polyethylene. Alternatively, other materials, such as stainless steel, may also be useful. In one embodiment, the friction ring 214 is secured to the catheter shaft 24 via an adhesive.

During use, the balloon adjustment sleeve 212 can be maneuvered to vary the effective balloon inflation length L1. As previously described, the proximal end 216 of the balloon adjustment sleeve 212 is preferably adhered to the distal portion 36 of the catheter shaft 24. Additionally, the proximal portion 218 of the balloon adjustment sleeve 212 interacts with the friction ring 214 such that one of the series of slots 224 selectively engages the friction ring 214. Thus, upon determination of a desired balloon inflation length, the distal portion 220 and the distal end 222 of the balloon adjustment sleeve 212 are co-axially slid along the distal portion 36 of the catheter shaft 24 and the balloon 26 to a position effectuating the effective balloon inflation length L1 equivalent to the desired balloon inflation length.

The proximal portion 218 of the balloon adjustment sleeve 212 facilitates this movement as the proximal portion 218 can be maneuvered such that a different one of the series of slots 224 engages the friction ring 214. Thus, the series of slots 224 formed by the proximal portion 218 of the balloon adjustment sleeve 212 in conjunction with the friction ring 214 serves as an attachment means for selectively securing the distal end 222 of the balloon adjustment sleeve 212 relative to the balloon 26. Upon inflation, the distal portion 220 and the distal end 222 of the balloon adjustment sleeve 212 restrict inflation of the balloon 26 proximal the distal end 222 to achieve the desired effective balloon inflation length L1.

Figure 8:
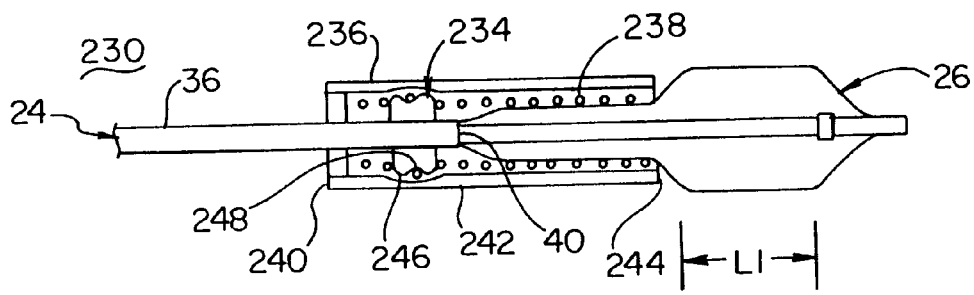
FIG. 8 is a partial, longitudinal cross-sectional view of the distal portion of a balloon catheter including an alternative embodiment of an adjustment device in accordance with the present invention.

Yet another alternative embodiment of a balloon catheter assembly 230 is shown in FIG. 8. Similar to previous embodiments, the balloon catheter assembly includes the catheter shaft 24, having the distal portion 36, and the balloon 26 fluidly connected to the distal end 40 of the catheter shaft 24. Additionally, the balloon catheter assembly 230 includes a balloon adjustment sleeve 232 co-axially received over the distal portion 36 of the catheter shaft 24 and a spool ring 234 secured to the distal portion 36 of the catheter shaft 24.

The balloon adjustment sleeve 232 includes an outer sleeve 236 and a coil 238. The outer sleeve 236 is a tubular body having an inner diameter slightly greater than an outer diameter of the catheter shaft 24 and includes a proximal end 240, an intermediate portion 242 and a distal end 244. In a preferred embodiment, the outer sleeve 236 is made of a relatively rigid, surgically-safe material such as SURLYN. Alternatively, other relatively rigid materials are equally acceptable.

The coil 238 is configured to have an inner diameter slightly greater than an outer diameter of the distal portion 36 of the catheter shaft 24. Further, the coil 238 preferably has a length approximately equal to that of the outer sleeve 236. With this configuration, the coil 238 is sized to extend along an interior of the intermediate portion 242 of the outer sleeve 236. Further, the coil 238 is secured at the proximal end 240 and the distal end 244 of the outer sleeve 236 by a weld. Alternatively, an adhesive or other attachment means can be used to secure the coil 238 to the intermediate portion 242 of the outer sleeve 236. In a preferred embodiment, the coil 238 is made of a rigid material, such as stainless steel. Alternatively, other rigid materials, such as nitinol, may also be useful.

The spool ring 234 is preferably sized to extend from the distal portion 36 of the catheter shaft 24 in a concentric fashion and includes a proximal wall 246, a platform 248 and a distal wall 250. As shown in FIG. 8, the proximal wall 246 and the distal wall 250 have an outer diameter greater than that of the platform 248. These components combine such that the spool ring 234 is preferably constructed to receive the coil 238 in the outer sleeve 236 in a rotatable fashion. In a preferred embodiment, the spool ring 234 is made of a relatively rigid material, such as stainless steel. Alternatively, other materials such as nitinol, nylon or PET may also be useful. As shown in FIG. 8, the spool ring 234 is secured to the distal portion 36 of the catheter shaft 24 near the distal end 40, preferably by an adhesive.

The balloon catheter assembly 230 functions in a manner highly similar to previous embodiments in that the effective balloon inflation length L1 can easily be adjusted. In this regard, the balloon adjustment sleeve 232, including the coil 238, is co-axially placed over the distal portion 36 of the catheter shaft 24. Upon determination of a desired balloon inflation length, the balloon adjustment sleeve 232 is maneuvered relative to the distal portion 36 of the catheter shaft 24 and the balloon 26. More particularly, the balloon adjustment sleeve 232 can be positioned such that an individual ring of the coil 238 is positioned on the platform 248. Under normal conditions, the proximal wall 246 and the distal wall 250 of the spool ring 234 prevents that particular ring of the coil 238 from disengaging the spool ring 234. However, a physician can rotate the balloon adjustment sleeve 232 such that the engaged ring of the coil 238 rotates off of the proximal wall 246, or the distal wall 250, and a different ring of the coil 238 is substituted therefor. With this allowed movement, the balloon adjustment sleeve 232 can be positioned such that the distal end 244 of the outer sleeve 236 is positioned over the balloon 26 so as to provide an effective balloon inflation length L1 equivalent to the desired balloon inflation length.

Once properly positioned, the balloon catheter assembly 230 is ready for deployment. In this regard, the balloon catheter assembly 230 may include a radiopaque marker 232 along the catheter shaft 24 and/or at an interior of the balloon 26 to assist in determining positioning of the balloon 26 at a treatment site. Upon inflation of the balloon 26, the outer sleeve 236, in conjunction with the coil 238, restricts inflation of the balloon 26 proximal the distal end 244 of the outer sleeve 236. Additionally, the spool ring 234 and the coil 238 interact as an attachment means to selectively secure the outer sleeve 236 relative to the distal portion 36 of the catheter 24 and the balloon 26.

Figure 9:
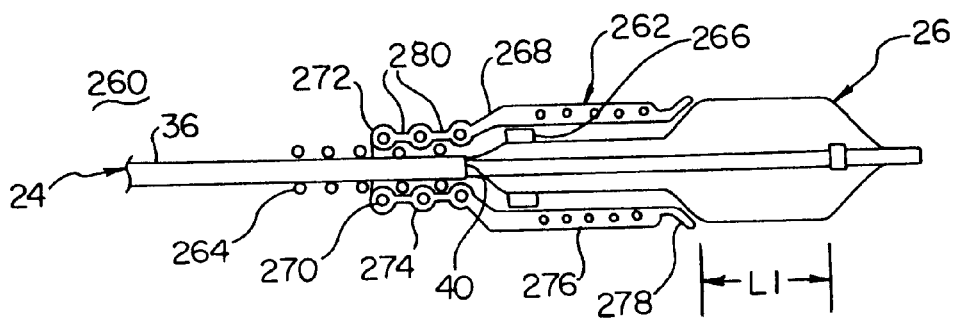
FIG. 9 is a partial, longitudinal cross-sectional view of the distal portion of a balloon catheter including an alternative embodiment of an adjustment device in accordance with the present invention.

Yet another embodiment of a balloon catheter assembly 260 is shown in FIG. 9. Similar to previous embodiments, the balloon catheter assembly 260 includes the catheter shaft 24, having the distal portion 36, and the balloon 26 fluidly connected to the distal end 40 of the catheter shaft 24. Additionally, the balloon catheter assembly 260 includes a balloon adjustment sleeve 262, an engagement coil 264 and a locking ring 266. As described in greater detail below, the balloon adjustment sleeve 262 is configured to be co-axially received over the catheter shaft 24. The engagement coil 264 is attached to an outer circumference of the distal portion 36 of the catheter shaft 24. Finally, the locking ring 266 is disposed at the distal end 40 of the catheter shaft 24.

The balloon adjustment sleeve 262 includes an outer sleeve 268 encompassing a series of rings 270. The outer sleeve 268 is similar to previous embodiments and is defined by a proximal end 272, a proximal portion 274, a distal portion 276 and a distal end 278. As shown in FIG. 9, the proximal portion 274 is configured to define a series of slots 280 between the rings 270. Further, the proximal portion 274 preferably has an inner diameter approximating an outer diameter of the distal portion 36 of the catheter shaft 24. The distal portion 276 of the outer sleeve 268 is configured to have an inner diameter slightly greater than an outer diameter of the distal portion 36 of the catheter shaft 24. Further, as shown in FIG. 9, the rings 270 within the distal portion 276 are more closely spaced. Thus, the distal portion 276 of the outer sleeve 268 is preferably less rigid than the proximal portion 274. Finally, the distal end 278 of the balloon adjustment sleeve 262 is preferably more elastic. Further, the distal end 278 is preferably flared relative to a remainder of the distal portion 276 and is made of a radiopaque material.

In a preferred embodiment, the adjustment sleeve 262 is formed by molding a relatively rigid polymer, such as urethane, about the series of rings 270. In this regard, the series of rings 270 are preferably made of a strong material such as tungsten.

The engagement coil 264 is sized to extend from the distal portion 36 of the catheter shaft 24 and is preferably made of a rigid material, such as stainless steel. Alternatively, other materials, such as PET, may also be useful for the engagement coil 264.

The locking ring 266 is preferably a ring-shaped body sized to extend from the distal end 40 of the catheter shaft 24. Alternatively, the locking ring 266 can be formed as a portion of the balloon 26. Regardless of exact location, the locking ring 266 includes an outer diameter slightly greater than an outer diameter of the engagement coil 264. In a preferred embodiment, the locking ring 266 is made of a relatively rigid material, such as stainless steel. Alternatively, other materials, such as PET, may also be useful.

Similar to previous embodiments, the balloon catheter assembly 260 provides for an adjustable effective balloon inflation length L1. The balloon adjustment sleeve 262 is co-axially received over the distal portion 36 of the catheter shaft 24 such that the proximal end 272 of the outer sleeve 268 engages the engagement coil 264 otherwise attached to the distal portion 36 of the catheter shaft 24. More particularly, the slots 280 formed by the proximal portion 274 of the outer sleeve 268 are appropriately sized to receive one rotation of the engagement coil 264. In effect, then, the engagement coil 264 and the proximal portion 274 of the outer ring 266 are threadably engaged such that the proximal portion 274 of the outer sleeve 268 can be moved in a threading fashion along the engagement coil 264.

Additionally, the distal portion 276 of the outer sleeve 268 selectively engages the locking ring 266. In this regard, the distal portion 276 of the outer sleeve 268 preferably has an inner diameter approximating an outer diameter of the locking ring 266. Thus, the balloon adjustment sleeve 262 is selectively secured to the distal portion 36 of the catheter shaft 24 via interaction of the proximal portion 274 of the outer sleeve 268 with the engagement coil 264; and interaction of the distal portion 276 of the outer sleeve 268 with the locking ring 266.

Upon determination of a desired balloon inflation length, the balloon adjustment sleeve 262 is maneuvered to position the distal end 278 of the outer sleeve 268 along the balloon 26 length to provide for the effective fluid inflation length L1 equivalent to the desired balloon inflation length. As previously described, the proximal portion 274 of the outer sleeve 268 can be maneuvered in a threading fashion either proximally or distally along the engagement coil 264. Movement of the proximal portion 274 imparts a movement onto the distal end 278 of the outer sleeve 268.

Upon inflation of the balloon 26, the distal end 278 of the outer sleeve 268 restricts inflation of the balloon 26 proximal the distal end 278. In this regard, the distal portion 276 of the outer sleeve 268 is relatively rigid to limit any expansion of the balloon 26. Notably, however, the distal portion 276 of the outer sleeve 268 has a diameter slightly larger than an outer diameter of the distal portion 36 of the catheter shaft 24 such that slight inflation of the balloon 26 proximal the distal end 278 of the outer sleeve 268 is allowed. As described with reference to previous embodiments, this slight inflation assists in preventing movement of the balloon adjustment sleeve 262, as opposing forces are applied to the distal end 278 of the outer sleeve 268. Thus, the engagement coil 264, the locking ring 268 and the series of rings 270 serve as an attachment means for selectively securing the outer sleeve 268 to the distal portion 36 of the catheter shaft 24. Finally, with the preferred flared, radiopaque configuration of the distal end 278, a physician can easily determine positioning of the balloon 26 via fluoroscopy.

The balloon catheter assembly of the present invention provides a variable length balloon feature while eliminating the drawbacks associated with prior art devices. In this regard, a relatively small adjustment device is disposed along the distal portion of the catheter shaft. The adjustment device includes an outer sleeve generally co-axially received over the distal portion of the catheter shaft. At least a portion of this outer sleeve is slidable relative to the catheter shaft and the balloon such the effective balloon inflation length can easily be selected and adjusted. Additionally, an attachment means is provided which selectively secures at least a portion of the outer sleeve to the distal portion of the catheter shaft such that the selected balloon inflation length will not change upon inflation. However, because the attachment means specifically provides for selective attachment of the outer sleeve to the distal portion of the catheter shaft, a physician can easily change the effective balloon inflation length to meet the demands presented by a particular treatment application.

New characteristics and advantages of the invention covered by this document have been set forth in the foregoing description. It will be understood that this disclosure, in many respects, is only illustrative. Changes may be made in details, particularly in matters of shape, size, and arrangement of parts, without exceeding the scope of the invention. The scope of the invention is, of course, defined in the language in which the appended claims are expressed. For example, a wire pull back can be provided extending from the outer sleeve to the proximal end of the catheter shaft. The wire pull back provides a physician with the ability to adjust positioning of the outer sleeve relative to the balloon from the proximal end of the catheter shaft.

What is claimed is:

1. A balloon catheter assembly including a catheter shaft having a distal portion terminating at a distal end, a balloon fluidly connected to the distal end of the catheter shaft, and an adjustment device disposed along the distal portion of the catheter shaft for adjusting effective balloon inflation length, the adjustment device comprising:

an outer sleeve generally having a distal end co-axially received over the distal portion of the catheter shaft, at least a portion of the outer sleeve being slidable relative to the distal portion of the catheter shaft, the distal end of the outer sleeve being configured to restrict inflation of the balloon proximal the distal end of the outer sleeve; and attachment means for selectively securing at least a portion of the outer sleeve to the distal portion of the catheter shaft such that the distal end of the outer sleeve is selectively maintained relative to the balloon to define a desired effective balloon inflation length, the attachment means including an enlarged shaft portion proximate the balloon and a locking sleeve generally co-axially received over the outer sleeve, the locking sleeve configured to selectively secure the outer sleeve to the enlarged shaft portion.

2. The adjustment device of claim 1, wherein the distal end of the outer sleeve includes a marker for providing a fluoroscopic indication of balloon positioning.

3. The adjustment device of claim 1, wherein the distal end of the outer sleeve includes a conical ring.

4. The attachment device of claim 1, wherein the distal end of the outer sleeve is configured to be an annular shoulder allowing at least partial inflation of the balloon both proximal and distal of the annular shoulder.

5. The adjustment device of claim 1, further comprising:

markers disposed along a distal portion of the catheter shaft for indicating effective balloon inflation length.

6. The adjustment device of claim 1, wherein the outer sleeve is configured to be adjusted when the balloon is in a deflated state, but cannot be adjusted when the balloon is in an inflated state.

7. A balloon catheter assembly including a catheter shaft having a distal portion terminating at a distal end, a balloon fluidly connected to the distal end of the catheter shaft, and an adjustment device disposed along the distal portion of the catheter shaft for adjusting effective balloon inflation length, the adjustment device comprising:

an outer sleeve generally having a distal end co-axially received over the distal portion of the catheter shaft, at least a portion of the outer sleeve being slidable relative to the distal portion of the catheter shaft, the distal end of the outer sleeve being configured to restrict inflation of the balloon proximal the distal end of the outer sleeve; and attachment means for selectively securing at least a portion of the outer sleeve to the distal portion of the catheter shaft such that the distal end of the outer sleeve is selectively maintained relative to the balloon to define a desired effective balloon inflation length, the attachment means including a rib attached to the distal portion of the catheter shaft proximal the balloon, and a locking sleeve generally co-axially received over the outer sleeve, wherein the locking sleeve is configured to selectively secure the outer sleeve to the rib.

8. The adjustment device of claim 1, wherein the locking sleeve includes a proximal end, an intermediate portion and a distal end, the proximal end of the locking sleeve having a diameter less than an outer diameter of the rib, and the distal end of the locking sleeve having a diameter greater than the diameter of the proximal end of the locking sleeve and approximating the outer diameter of the rib.

9. The adjustment device of claim 8, wherein the intermediate portion of the locking sleeve expands from the proximal end of the locking sleeve to the distal end of the locking sleeve such that the locking sleeve is configured to frictionally secures the outer sleeve to the rib.

10. The adjustment device of claim 7, wherein the rib is a ring attached to the distal portion of the catheter shaft.

11. The adjustment device of claim 10, wherein the ring includes an inner portion and an outer portion, the outer portion being plastic.

12. The adjustment device of claim 7, wherein the outer sleeve includes a stop collar positioned on a proximal end thereof, the stop collar being configured to prevent the outer sleeve from disengaging the catheter shaft.

13. The adjustment device of claim 12, wherein the stop collar is a rigid body having an inner diameter less than an outer diameter of the rib.

14. The adjustment device of claim 7, wherein the outer sleeve is a relatively flexible body having a relatively rigid distal end such that the outer sleeve permits slight inflation of the balloon proximal the distal end of the outer sleeve.

15. The adjustment device of claim 14, wherein the outer sleeve is defined by a proximal portion and a distal portion, the distal portion having a diameter greater than a diameter of the proximal portion.

16. An improved balloon catheter including a balloon fluidly connected to a distal end of a catheter shaft, the improvement comprising:

an outer sleeve generally co-axially received over a distal portion of the catheter shaft, the outer sleeve including a proximal end, an intermediate portion and a distal end sized to restrict balloon inflation proximal the distal end, and at least a portion of the intermediate portion being slidable relative to the catheter shaft for an adjusting effective balloon inflation length; and attachment means positioned proximate a distal end of the catheter shaft for selectively securing the distal end of the outer sleeve to the catheter shaft, the attachment means including an enlarged shaft portion proximate the balloon and a locking sleeve generally co-axially received over the outer sleeve, the locking sleeve configured to selectively secure the outer sleeve to the enlarged shaft portion.

17. The improved balloon catheter of claim 16, wherein the distal end of the outer sleeve is configured to be an annular shoulder, allowing at least partial inflation of the balloon both proximal and distal of the annular shoulder.

18. An improved balloon catheter including a balloon fluidly connected to a distal end of a catheter shaft, the improvement comprising:

an outer sleeve generally co-axially received over a distal portion of the catheter shaft, the outer sleeve including a proximal end, an intermediate portion and a distal end sized to restrict balloon inflation proximal the distal end, and at least a portion of the intermediate portion being slidable relative to the catheter shaft for adjusting effective balloon inflation length; and attachment means positioned proximate a distal end of the catheter shaft for selectively securing the distal end of the outer sleeve to the catheter shaft, the attachment means including a rib attached to the distal portion of the catheter shaft proximal the balloon, and a locking sleeve configured to be generally co-axially received over the outer sleeve and configured to selectively secure the outer sleeve to the rib.

19. The improved balloon catheter of claim 18, wherein the locking sleeve includes a proximal end, an intermediate portion and a distal end, the proximal end of the locking sleeve having a diameter smaller than a diameter of the rib, and the distal end of the locking sleeve having a diameter greater than the diameter of the proximal end of the locking sleeve and approximating the diameter of the rib.

20. The improved balloon catheter of claim 18, wherein the outer sleeve includes a stop collar positioned at the proximal end, the stop collar being configured to prevent the outer sleeve from disengaging the catheter shaft.

21. A method of using a variable length balloon catheter, the method comprising:

providing a catheter shaft including a distal portion, and having a balloon fluidly connected to a distal end thereof;

providing an adjustment device including:

an outer sleeve generally co-axially received over the distal portion of the catheter shaft and including a sleeve distal end for restricting balloon inflation proximal the sleeve distal end;

attachment means for selectively securing the outer sleeve to the distal portion of the catheter shaft, the attachment means including an enlarged shaft portion proximate the balloon, and a locking sleeve generally co-axially received over the outer sleeve, the locking sleeve configured to selectively secure the outer sleeve to the enlarged shaft portion;

determining a desired balloon inflation length;

sliding the outer sleeve along the distal portion of the catheter shaft and a portion of the balloon such that the sleeve distal end defines an effective balloon inflation length approximating the desired balloon inflation length;

securing the outer sleeve to the distal portion of the catheter shaft by sliding the locking sleeve over the outer sleeve and the enlarged shaft portion until the outer sleeve is secured between the locking sleeve and the enlarged shaft portion; and directing the balloon to a treatment site.

22. The method of claim 21, wherein securing the outer sleeve of the catheter shaft includes securing the outer sleeve proximate a distal end of the catheter shaft.

23. The method of claim 21, wherein the outer sleeve is secured to the distal portion of the catheter shaft such that the outer sleeve cannot be moved upon directing the balloon to the treatment site.

24. The method of claim 21, wherein determining a desired balloon inflation length includes measuring a length of a stent to be delivered to the treatment site.

25. The method of claim 24, further comprising:

securing the stent over the balloon prior to inflation.

* * * * *